(12) United States Patent
Geistert

(10) Patent No.: US 8,239,040 B2
(45) Date of Patent: Aug. 7, 2012

(54) ELECTRODE CATHETER FOR INTERVENTION PURPOSES

(75) Inventor: Wolfgang Geistert, Rheinfelden (DE)

(73) Assignee: Biotronik CRM Patent AG, Baar (CH)

( * ) Notice: Subject to any disclaimer, the term of this patent is extended or adjusted under 35 U.S.C. 154(b) by 1170 days.

(21) Appl. No.: 11/863,319

(22) Filed: Sep. 28, 2007

(65) Prior Publication Data

US 2008/0119917 A1   May 22, 2008

(30) Foreign Application Priority Data

Nov. 17, 2006 (DE) .................. 10 2006 054 620
Jul. 2, 2007 (DE) .................. 10 2007 030 678
Jul. 26, 2007 (DE) .................. 10 2007 034 990

(51) Int. Cl.
*A61B 5/055* (2006.01)
*A61N 1/05* (2006.01)

(52) U.S. Cl. ....................... 607/116; 600/411

(58) Field of Classification Search .............. 607/115, 607/116; 600/372–374; 606/13–17
See application file for complete search history.

(56) References Cited

U.S. PATENT DOCUMENTS

| | | | |
|---|---|---|---|
| 6,348,070 B1 * | 2/2002 | Teissl et al. | 623/11.11 |
| 6,718,207 B2 * | 4/2004 | Connelly | 607/9 |
| 6,944,489 B2 | 9/2005 | Zeijlemaker et al. | |
| 6,993,373 B2 | 1/2006 | Vrijheid et al. | |
| 7,610,101 B2 * | 10/2009 | Wedan et al. | 607/116 |
| 7,738,942 B2 * | 6/2010 | Weiner et al. | 600/411 |
| 2002/0095084 A1 * | 7/2002 | Vrijheid et al. | 600/411 |
| 2002/0138102 A1 | 9/2002 | Weiner et al. | |
| 2002/0198569 A1 | 12/2002 | Foster et al. | |
| 2003/0144720 A1 | 7/2003 | Villaseca | |
| 2003/0144721 A1 | 7/2003 | Villaseca | |
| 2005/0222658 A1 | 10/2005 | Hoegh et al. | |
| 2005/0288751 A1 | 12/2005 | Gray | |
| 2005/0288752 A1 | 12/2005 | Gray | |
| 2005/0288754 A1 | 12/2005 | Gray | |
| 2005/0288756 A1 | 12/2005 | Gray | |
| 2006/0009819 A1 | 1/2006 | Przybyszewski | |
| 2006/0200218 A1 | 9/2006 | Wahlstrand | |

FOREIGN PATENT DOCUMENTS

WO   WO 2007/118194   10/2007

OTHER PUBLICATIONS

European Search Report, dated Dec. 20, 2007.
German Search Report, dated Aug. 13, 2007.
German Search Report, dated Apr. 1, 2008.

* cited by examiner

*Primary Examiner* — Carl H Layno
*Assistant Examiner* — Allen Porter, Jr.
(74) *Attorney, Agent, or Firm* — ARC IP Law, PC; Joseph J. Mayo

(57) ABSTRACT

An electrode catheter that includes an elongate electrode catheter body having a distal end and a proximal end, at least one electrode pole in the area of the distal end of the electrode body, and at least one supply line, which runs insulated in the electrode body in the main direction (H) from the proximal end to the distal end, to the at least one electrode pole, wherein the at least one supply line is configured to desensitize the electrode catheter to the radiation of an electromagnetic field of an interfering frequency having a specific wavelength($\lambda$), with the supply line changing its run direction at least twice in such a way that it runs at least once opposite to the main direction (H), the distance (L1,L2) between two direction changes (R) is shorter than half of the wavelength ($\lambda/2$) of the interfering frequency.

17 Claims, 1 Drawing Sheet

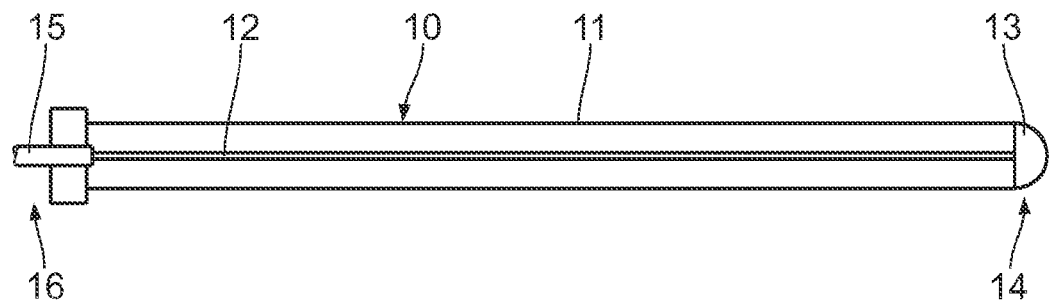
Fig. 4
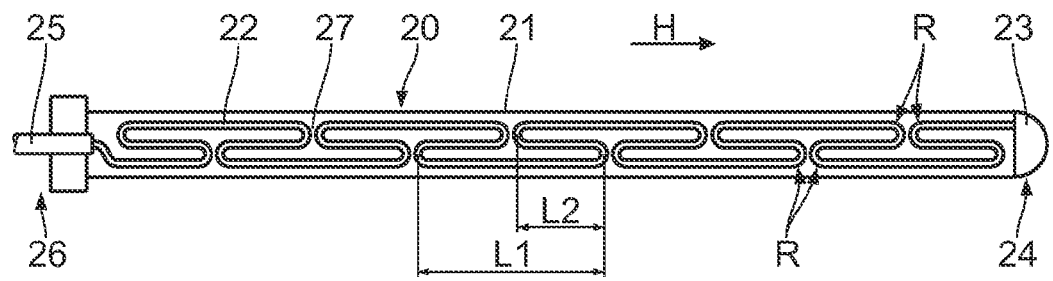
Fig. 1
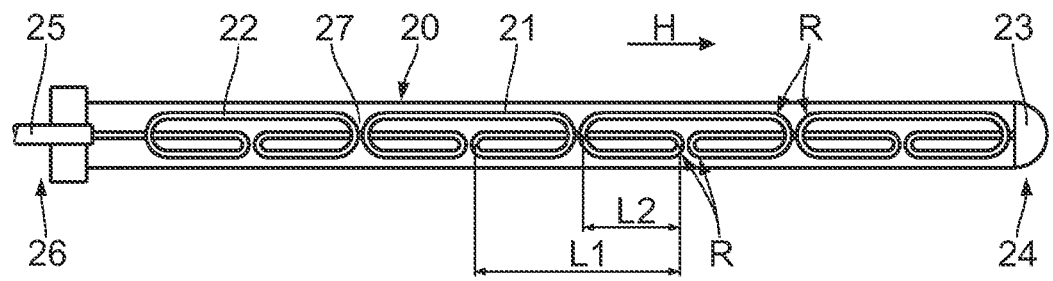
Fig. 2
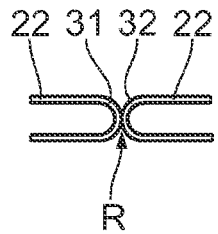 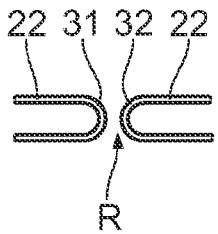 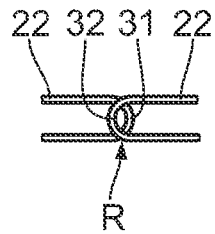 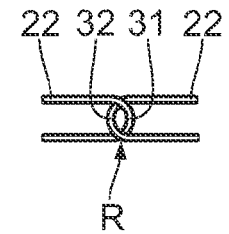
Fig. 3a    Fig. 3b    Fig. 3c    Fig. 3d

ELECTRODE CATHETER FOR INTERVENTION PURPOSES

This application takes priority from German Patent Application DE 10 2006 054 620.2 filed 17 Nov. 2006, German Patent Application DE 10 2007 030 678.6 filed 2 Jul. 2007 and German Patent Application DE 10 2007 034 990.6 filed 26 Jul. 2007, the specifications of which are all hereby incorporated herein by reference.

BACKGROUND OF THE INVENTION

1. Field of the Invention

The present invention relates to an electrode catheter for intervention purposes, such as a cardiac pacemaker, neurostimulator, ICD electrode, or EP catheter. The term "electrode catheter" is to be understood as all types of elongate implants which comprise at least one wire enclosed in the elongate body of the implant and running largely insulated from the patient therein using at least one surrounding medium, which is in direct or indirect electrical contact with the surrounding medium (e.g., body tissue) in proximity to the distal end. In addition to the above-mentioned types, for example, electrophysiological diagnostic catheters, ablation catheters, and pacemaker electrodes may also be cited.

2. Description of the Related Art

Electrode catheters of this type are known to have an elongate body having a distal end and a proximal end. At least one electrode pole is provided in the area of the distal end, which is typically used for discharging intervention pulses or perceiving cardiac, nerve, or brain signals. This electrode pole is designed, for example, as a tip electrode situated directly on the distal end, as a ring pole placed at a distance therefrom, or as a shock electrode. The intervention pulses discharged via this pole are the pacemaker pulses of a cardiac pacemaker or neurostimulator, a high-voltage pulse in the case of a defibrillator, or an ablation energy pulse in the case of an ablation device, for example.

An insulated supply line runs to this electrode pole in the electrode body. Furthermore, such electrode catheters usually have further electrode poles, which are generally thus referred to, via which the supply line may come into electrical contact with tissue. A ring electrode pole of a bipolar electrode or an EP catheter is to be cited as an example. Furthermore, an electrode sheath, which encloses the at least one supply line, is provided in the electrode body for insulating the supply line.

In recent years, magnetic resonance diagnostic devices have gained significantly in importance because of their examination methodology, which is gentle to patients, non-invasive, and completely free of pain and side effects. Typical electrode catheters display the problem that electrode catheters of this type strongly heat the tissue in magnetic resonance diagnostic devices under the influence of the electromagnetic radiation generated thereby because of electromagnetic induction and the discharge of the induced energy in the area of their contact surface(s) to the tissue. The reason for this is particularly in the solid, metallic supply lines to the electrode poles, which act as antennas and in which, because of their insulation, the antenna currents induced by high-frequency (HF) fields may only be dissipated into the body electrolytes at the electrode poles, which form the electrical interface to the tissue. The cited HF fields operate, for example, in an operating frequency range of 64 MHz for a 1.5 Tesla MR tomograph. Because extremely strong heating of the tissue may occur in proximity to the electrode poles, the access to magnetic resonance diagnostic devices is typically blocked to wearers of cardiological and neurological intervention devices, such as cardiac pacemakers, neurostimulators, or defibrillators. Electrophysiological examinations and interventions, such as ablations, are also not possible in MR devices.

To prevent or minimize the hazardous heating of the body cells, the maximum antenna currents must be limited or reduced. Known solutions suggest discrete components for this purpose, which act as a band-stop filter or as a low-pass filter and thus limit the longitudinal current of the antenna for the frequencies of interest or, in other words, increase the longitudinal resistance of the antenna. Other solutions suggest capacitors which are connected in parallel to the insulation and thus dissipate the antenna current.

In this regard, for example, U.S. Pat. No. 6,944,489, US 2003/0144720, US 2003/0144721, US 2005/0288751 A1 (and the simultaneously published parallel publications US 2005/0288752 A1, US 2005/0288754 A1, and US 2005/0288756 A1, which have essentially the same wording) are cited.

US 2006/0009819 A1 discloses a cardiac pacemaker having an elongate electrode which is connected to a pulse generator connector. A passive lossy circuit is provided, which is electrically connected between a distal section of the electrode supply line and a high-frequency grounded surface. The passive lossy circuit has a high-frequency impedance which is approximately equal to a characteristic impedance of the electrode in its implanted state in the body. The reflection of incident waves is thus minimized at the terminals of the lossy circuit and their energy is intentionally dissipated here. The passive lossy circuit also acts as a low-pass filter, because of which the electrode is functional in normal operation of the cardiac pacemaker.

The known solutions have the disadvantage that discrete components complicate the production and thus make it costly. In addition, such discrete components reduce the reliability and long-term stability of electrode catheters, which is particularly disadvantageous if they are provided as long-term implants. Finally, discrete components, such as inductors and resistors, require a certain overall size if they are provided for high-current applications, such as defibrillators and HF ablation. This is contrary to the attempts to design an implant as especially small and slim.

BRIEF SUMMARY OF THE INVENTION

On the basis of the problems described, the present invention is based on the object of implementing electrode catheters in such a way that they are designed having a simple construction and are producible cost-effectively and may be placed in radiation fields of magnetic resonance diagnostic devices without relevant risk to the wearer. In particular, discrete components for solving the problems are to be avoided and the properties of the electrode in regard to its antenna characteristic are to be influenced in another way so that current concentrations and accordingly excess heating at electrode poles may not occur, in particular not around the tip of the electrode catheter. The electrode catheter provided is thus also to be suitable for high-current applications (ICD, ablation).

This object is achieved in that the at least one supply line running in the body of the electrode catheter changes its run direction at least twice in such a way that it runs opposite to the main direction at least once and the distance between two direction changes is shorter than half of the wavelength ($\lambda/2$) of the interfering frequency.

Due to this design, in regard to the stated object, the electrode catheter is desensitized to the radiation of an electromagnetic field of an interfering frequency having a specific wavelength, without the electrode catheter requiring separate discrete components.

The physical background of the present invention may be described as follows:

An elongate, electrical conductor becomes a poor antenna at a specific frequency f if it has a length which is less than half, but better less than a fourth of the wavelength λ at this frequency. The wavelength is a function of the surrounding material—in particular of its dielectric constant (permittivity) ∈ and permeability μ—in which the conductor is located, according to the following formula:

$$\lambda = \frac{1}{f \times \sqrt{\mu \varepsilon}}$$

The dielectric constant (permittivity) ∈ is composed of the natural constant $\varepsilon_0$ (8.854 ... *$10^{-12}$ As/Vm) and the relative dielectric constant (permittivity) $\varepsilon_R$ (∈=$\varepsilon_0 \times \varepsilon_R$). The permeability μ results from the natural constant $\mu_0$ (1.2566 ... *$10^{-6}$ kg*m/$A^2 s^2$) and the relative permeability $\mu_R$ (μ=$\mu_0 \times \mu_R$).

For body tissue, which primarily consists of water ($\mu_R$ approximately 80), for a frequency of 64 MHz, which is typical for 1.5 Tesla MR devices, one arrives at a wavelength λ of approximately 52 cm. λ/4 is thus approximately 13 cm.

In an electrode catheter according to the present invention, the supply line is thus divided into small sections, which are each shorter than half, preferably shorter than a fourth of the wavelength of the interfering radiation to which the electrode catheter is to be desensitized.

Depending on the degree of the required desensitization, these direction changes may extend over the entire length of the electrode catheter or also only over a partial length. The greatest desensitization is achieved if the direction changes extend over the entire length of the electrode catheter.

It is not the case that no voltage at all is induced in short antennas, i.e., antennas less than λ/4 long, which are located in an electromagnetic field. Therefore, it is advantageous if the length of the individual legs is dimensioned in such a way that the currents induced in the individual legs precisely cancel out due to their phase shift. For this purpose, they must have a certain length, however. The distance between two direction changes is therefore to be shorter than λ/2 on one hand, but is not to be shorter than λ/16 of the wavelength of the interfering frequency to which the electrode catheter is to be insensitive on the other hand.

A design in which the long legs of the sections of the supply line provided by the direction change have a length which corresponds to approximately λ/4 and in which the short legs have a length which corresponds to approximately λ/8 has proven to be advantageous. If the legs are shorter than these values, the induced voltages cancel out increasingly less ideally, the damping effect of the configuration worsens, and the currents exiting at the ends of the electrode catheter become larger again than in the cited ideal construction.

According to further preferred embodiments, the supply line may be laid meandering or looping, preferably additionally twisted or coiled, to implement the direction change. The supply line itself may fundamentally be implemented by any electrical conductor, i.e., for example as a wire, lead, coil, or printed circuit on a correspondingly configured substrate.

The electrode catheter according to the present invention may finally be optimized in connection with the supply line insulation in regard to extensive insensitivity to high-frequency interfering fields and improving usability in radiation fields of magnetic resonance diagnostic devices by designing the insulation in such a way that it ensures good coupling of the supply line to the surrounding body tissue at the interfering frequency. For this purpose, the insulation may be very thin, which allows capacitive coupling, but is often precluded for reasons of mechanical ruggedness. Alternatively or additionally, the insulation of the supply line may also be produced from a minimally-insulating material or a material insulating as a function of frequency. This measure is the subject matter of application DE 10 2007 022 333.3 of the applicant. Briefly summarized, the quality of the resonant circuit formed by the electrode catheter with the body is reduced enough by this measure that on one hand the energy absorbed by the antenna is reduced and on the other hand the losses are distributed in the overall formation of electrode supply line/insulation/body in such a way that excess current concentration does not occur at specific points.

BRIEF DESCRIPTION OF THE DRAWINGS

Further features, details, and advantages of the present invention result from the following description, in which exemplary embodiments are explained in greater detail on the basis of the attached drawings.

FIGS. 1 and 2 show schematic longitudinal sections of electrode catheters according to the present invention in two different embodiments, FIG. 3 shows detail views of supply lines at the points of their direction change in different configurations, and FIG. 4 shows a schematic longitudinal section of an electrode catheter according to the prior art.

DETAILED DESCRIPTION OF THE INVENTION

FIG. 4 schematically shows the prior art in the form a longitudinal section through an electrode catheter 10. The supply line 12 is essentially housed stretched in the shaft 11 of the electrode catheter 10. The supply line connects the electrode pole 13 at the distal end 14 of the electrode catheter to the connector 15, which produces the electrical connection to a device, at the proximal end 16 of the electrode catheter 10. Treatment devices such as implantable or external stimulators, cardiac pacemakers, or defibrillators are viewed as the device. However, diagnostic devices or combinations of treatment and diagnostic devices are also conceivable.

FIGS. 1 and 2 schematically show various embodiments of the configuration of a supply line 22 in the shaft 21 of an electrode catheter 20 according to the present invention. The supply line connects the electrode pole 23 at the distal end 24 of the electrode catheter to the connector 25 at the proximal end 26 of the electrode catheter. A meandering configuration is shown in FIG. 1, in which the supply line 22 changes its run direction in and opposite to the main direction H of the electrode catheter 20 multiple times. The direction changes R thus formed therefore result in long legs L1 and short legs L2 in the supply line 22. The length of the long leg L1 approximately corresponds to a fourth of the wavelength of the interfering frequency, i.e., λ/4. The length of the short leg L2 approximately corresponds to λ/8 of the wavelength of the interfering frequency.

For an electrode catheter which is to be insensitive to a frequency of 64 MHz, the insulated supply line 22 thus runs, for example, beginning from the distal tip, 7 cm in the proximal direction, the supply line 22 is then folded by approximately 180° and again runs 6.5 cm in the distal direction, the supply line 22 is then folded again and now runs 13 cm in the proximal direction, then 6.5 cm back in the distal direction, then 13 cm back in the proximal direction, etc., until the supply line 22 reaches the proximal end 25 of the electrode catheter 20.

A looped configuration of the supply line 22 is shown in FIG. 2, in which the individual legs L1 and L2 of the supply line 22 obtain the recognizable loop shape by corresponding direction changes R. Otherwise, the statements in regard to FIG. 1 apply for the antenna effect of the supply line.

Furthermore, for both variants shown in FIGS. 1 and 2, the insulation of the supply line 22 identified as a whole by 27 comprises a material insulating as a function of frequency, because of which the quality of the antenna effect worsens and the electrode catheter absorbs less interfering energy and, in addition, further dissipation and thus distribution of the energy irradiated into the electrode catheter by an interfering frequency result.

In further embodiment (not shown), the legs of the supply line meanders or loops are twisted with one another or the entire supply line laid as described is shaped into a coil.

Furthermore, it is to be ensured that the legs and tips of the supply line 22, which lie adjacent to one another and intersect, do not electrically contact, to prevent a short circuit. This may be performed in that the supply lines receive individual insulation made of lacquer or a polymer, for example, (e.g., a Teflon coating). In another embodiment, the legs run in different lumens of the catheter shaft. The individual insulation of the supply line 22 is not shown in the figures.

The supply line 22 may itself be a wire, a lead made of multiple wires, a coil made of one or more wires, or a printed circuit applied to a carrier. The meanders or loops may be produced by corresponding guiding of the wire or the leads or by connecting the ends of individual stretched or coiled conductor pieces of the leg length L1 or L2 using soldering, welding, crimping, etc.

FIG. 3 schematically shows possible embodiments of the meander/loop end configuration of an electrode catheter 20 according to the present invention in the area of two neighboring direction changes R of the supply line 22. In FIG. 3a, the tips 31, 32 of the meander/loop ends contact. In FIG. 3b, the tips 31, 32 of the meander/loop ends do not contact. In FIG. 3c, the tips 31, 32 of the meander/loop ends overlap, while in FIG. 3d, the tips 31, 32 of the meander/loop ends are intertwined. In all cases, however, the above-mentioned galvanic separation between the coils of the supply line 22 is to be ensured.

What is claimed is:

1. An electrode catheter for intervention purposes, configured to coupled with a cardiac pacemaker, neurostimulator, ICD electrode, or EP catheter, comprising:
   an electrode body (20) comprising an elongate electrode catheter body (21) having a distal end (24) and a proximal end (26);
   at least one electrode pole (23) in an area of said distal end (24) of said electrode body (20);
   at least one supply line (22), which runs insulated in said electrode body (21) in a main direction (H) from said proximal end to said distal end, to said at least one electrode pole (23);
   wherein to desensitize said electrode catheter to radiation of an electromagnetic field radiated by a magnetic resonance diagnostic device of an interfering frequency having a specific wavelength ($\lambda$), said at least one supply line (22) changes run direction at least twice so that three portions of said at least one supply line are situated in a longitudinal portion of said electrode body where said run direction changes at least twice in such a way that said at least one supply line (22) runs at least once opposite to said main direction (H) and twice along said main direction (H), and a distance (L2) between two direction changes (R) is shorter than approximately half of a wavelength ($\lambda/2$) of said interfering frequency; and,
   wherein said at least one supply line comprises no discrete components including inductors or capacitors within said electrode body (21).

2. The electrode catheter according to claim 1, wherein said distance(L2) between said two direction changes (R) corresponds at most to a fourth of said wavelength ($\lambda/4$) of said interfering frequency.

3. The electrode catheter according to claim 1, wherein said distance (L2) between two sequential direction changes (R) of said at least one supply line (22) is greater than a sixteenth of said wavelength ($\lambda/16$) of said interfering frequency.

4. The electrode catheter according to claim 1, wherein said at least one supply line (22) has multiple direction changes (R) along its course.

5. The electrode catheter according to claim 1 wherein said at least one supply line (22) comprises direction changes (R) of alternating long and short legs (L1, L2), wherein a length of said long legs (L1) corresponds to approximately a fourth of said wavelength ($\lambda/4$) of said interfering frequency and wherein a length of said short legs (L2) corresponds to approximately an eighth of said wavelength ($\lambda/8$) of said interfering frequency.

6. The electrode catheter according to claim 1, wherein said at least one supply line (22) is laid meandering or looped in its course because of direction changes (R).

7. The electrode catheter according to claim 6, wherein said at least one supply line (22) is additionally twisted or coiled in its course to form coils.

8. The electrode catheter according to claim 1, wherein said at least one supply line (22) is implemented as a wire, lead, coil, or printed circuit.

9. The electrode catheter according to claim 7, wherein said coils of said at least one supply line (22) do not contact, are contacted, overlap, or intertwine in an area of two neighboring direction changes (R).

10. The electrode catheter according to claim 1, further comprising insulation (27) associated with said at least one supply line (22) that comprises a minimally-insulating material or a material that insulates as a function of frequency.

11. An electrode catheter for intervention purposes, configured to coupled with a cardiac pacemaker, neurostimulator, ICD electrode, or EP catheter, comprising:
   an electrode body (20) comprising an elongate electrode catheter body (21) having a distal end (24) and a proximal end (26);
   at least one electrode pole (23) in an area of said distal end (24) of said electrode body (20);
   at least one supply line (22), which runs insulated in said electrode body (21) in a main direction (H) from said proximal end to said distal end, to said at least one electrode pole (23) wherein said at least one supply line (22) is divided by multiple direction changes (R) into alternating long and short legs (L1, L2), wherein a length of said long legs (L1) corresponds to approximately a fourth of said wavelength ($\lambda/4$) of said interfering frequency and wherein a length of said short legs (L2) corresponds to approximately an eighth of said wavelength ($\lambda/8$) of said interfering frequency;
   wherein to desensitize said electrode catheter to radiation of an electromagnetic field radiated by a magnetic resonance diagnostic device of an interfering frequency having a specific wavelength (λ), said at least one supply line (22) changes run direction at least twice so that three portions of said at least one supply line are situated in a portion of said electrode body where said run direction changes at least twice in such a way that said at least one supply line (22) runs at least once opposite to said main direction (H) and twice along said main direction (H), and a distance (L2) between two direction changes (R) is shorter than approximately half of a wavelength (λ/2) of said interfering frequency; and, wherein said at least one supply line (22) comprises no discrete components including inductors or capacitors within said electrode body (21).

12. The electrode catheter according to claim 11, wherein said distance (L2) between said two direction changes (R) corresponds at most to a fourth of said wavelength (λ/4) of said interfering frequency.

13. The electrode catheter according to claim 11, wherein said distance (L2) between two sequential direction changes (R) of said at least one supply line (22) is greater than a sixteenth of said wavelength (λ16) of said interfering frequency and wherein energy absorbed by said at least one supply line occurs along lengths of greater than said sixteenth (λ/16) of said wavelength of said interfering frequency.

14. The electrode catheter according to claim 11, wherein said at least one supply line (22) is laid meandering or looped in its course because of direction changes (R).

15. The electrode catheter according to claim 14, wherein said at least one supply line (22) is additionally twisted or coiled in its course to form coils.

16. The electrode catheter according to claim 15, wherein said coils of said at least one supply line (22) do not contact, are contacted, overlap, or intertwine in an area of two neighboring direction changes (R).

17. The electrode catheter according to claim 11, wherein said at least one supply line (22) is implemented as a wire, lead, coil, or printed circuit.

* * * * *